United States Patent
Fruge et al.

(12) 
(10) Patent No.: US 8,974,772 B2
(45) Date of Patent: Mar. 10, 2015

(54) TWO PHASE TOOTHPASTE COMPOSITION

(75) Inventors: Linh Fruge, Hillsborough, NJ (US);
James R. Brown, Edison, NJ (US);
Susan Herles, Flemington, NJ (US);
Kimberlee Panaligan, Parlin, NJ (US);
Evangelia S. Arvanitidou, Princeton, NJ (US); Nebojsa Milanovich, Issaquah, WA (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 1118 days.

(21) Appl. No.: 11/023,968

(22) Filed: Dec. 28, 2004

(65) Prior Publication Data
US 2006/0140879 A1    Jun. 29, 2006

(51) Int. Cl.
A61K 8/00     (2006.01)
A61K 8/21     (2006.01)
A61K 8/19     (2006.01)
A61K 8/34     (2006.01)
A61Q 11/00    (2006.01)

(52) U.S. Cl.
CPC ... *A61K 8/21* (2013.01); *A61K 8/19* (2013.01); *A61K 8/347* (2013.01); *A61K 2800/88* (2013.01); *A61Q 11/00* (2013.01)
USPC .......................................................... 424/49

(58) Field of Classification Search
None
See application file for complete search history.

(56) References Cited

U.S. PATENT DOCUMENTS

| | | | |
|---|---|---|---|
| 5,217,710 A * | 6/1993 | Williams et al. ................ 424/52 |
| 5,288,480 A | 2/1994 | Gaffar et al. |
| 5,348,733 A | 9/1994 | Morishima et al. |
| 5,487,906 A * | 1/1996 | Dixit et al. .................... 424/673 |
| 5,538,715 A | 7/1996 | Gaffar et al. |
| 5,578,293 A * | 11/1996 | Prencipe et al. ................ 424/49 |
| 5,693,314 A * | 12/1997 | Campbell et al. ............... 424/49 |
| 5,716,600 A | 2/1998 | Zahradnik et al. |
| 5,776,435 A | 7/1998 | Gaffar et al. |
| 5,843,406 A | 12/1998 | Mordarski et al. |
| 5,855,874 A | 1/1999 | Gopalkrishnan et al. |
| 5,976,508 A | 11/1999 | Nabi et al. |
| 5,980,869 A | 11/1999 | Sanker et al. |
| 5,985,249 A | 11/1999 | Fischer |
| 6,106,812 A | 8/2000 | Prencipe et al. |
| 6,110,446 A * | 8/2000 | Prencipe et al. ................ 424/53 |
| 6,120,754 A | 9/2000 | Lee et al. |
| 6,187,295 B1 | 2/2001 | Glandorf |
| 6,214,321 B1 | 4/2001 | Lee et al. |
| 6,261,540 B1 | 7/2001 | Nelson |
| 6,306,370 B1 | 10/2001 | Jensen et al. |
| 6,309,625 B1 | 10/2001 | Jensen et al. |
| 6,368,576 B1 | 4/2002 | Jensen et al. |
| 6,447,757 B1 | 9/2002 | Orlowski et al. |
| 6,488,913 B2 | 12/2002 | Orlowski et al. |
| 6,509,007 B2 | 1/2003 | Rajaiah et al. |
| 6,521,216 B1 * | 2/2003 | Glandorf et al. ............... 424/52 |
| 6,559,189 B2 | 5/2003 | Baker, Jr. et al. |
| 6,635,676 B2 | 10/2003 | Baker, Jr. et al. |
| 6,696,043 B2 | 2/2004 | Orlowski et al. |
| 6,713,049 B1 | 3/2004 | White, Jr. et al. |
| 2003/0206874 A1 | 11/2003 | Doyle et al. |
| 2005/0271601 A1 * | 12/2005 | Milanovich et al. ............ 424/49 |

FOREIGN PATENT DOCUMENTS

| | | |
|---|---|---|
| EP | 0 696 450 | 2/1996 |
| EP | 1178773 | 8/2005 |
| GB | 2 227 660 | 8/1990 |
| GB | 2392917 | 3/2004 |
| WO | 99/47108 | 9/1999 |
| WO | 02/02128 | 1/2002 |
| WO | WO 00/62749 | 2/2002 |

OTHER PUBLICATIONS

"Fluoride". Wikipedia encyclopedia. Retrieved May 10, 2006. <http://en.wikipedia.org/wiki/Fluoride>.
Search Report from Corresponding PCT Application No. PCT/US2005/042161 Mailed on Jun. 13, 2006.

* cited by examiner

*Primary Examiner* — Snigdha Maewall
(74) *Attorney, Agent, or Firm* — Howard C. Lee

(57) ABSTRACT

An oral care composition having a first phase of clinically efficacious 2,4,4'-trichloro 2'-hydroxydiphenyl ether admixed in a first orally acceptable aqueous vehicle, and a second phase having a stannous salt (such as stannous fluoride) admixed in a second orally acceptable aqueous vehicle. The second phase has no less than 10 molar percent of soluble stannous ion respective to a mathematical sum of moles of the soluble stannous ion and moles of the stannous salt in the second phase. In one embodiment, the two phases are provided in a dual-tube toothpaste oral care kit.

20 Claims, No Drawings

TWO PHASE TOOTHPASTE COMPOSITION

The present invention relates to dentifrice compositions useful for cleaning teeth. In particular, the present invention includes two phase dentifrice compositions.

Oral care compositions are used for a wide variety of purposes, including for enhancing personal health, hygiene, and appearance, as well as for preventing or treating a variety of diseases and other conditions in humans and in animals.

The formulation of such compositions presents a number of challenges. They must be pharmaceutically and/or cosmetically acceptable for their intended use. Compositions that contain therapeutic active materials preferably deliver the active at effective levels, avoiding undue chemical degradation. Similarly, compositions containing cosmetically functional materials must deliver the material to the oral cavity at effective levels under the conditions that they are typically used by the consumer.

Moreover, the aesthetic appeal of all such compositions is important, and can have significant effects on consumer acceptance and usage. Aesthetic effects have been acknowledged to play an important role in consumer acceptance of many products. Although such products have met with consumer approval, the art seeks to further improve the aesthetic effects as well as the cosmetic and therapeutic benefits of these products. Indeed, many such compositions known in the art are deficient in one or more attributes. Thus, there is an ongoing need for new oral care compositions, and methods of their use.

A variety of active materials are disclosed in the art for use in oral care compositions, including fluoride salts and antimicrobial agents. Among the fluoride salts is stannous fluoride, which provides both fluoride ions for efficacy in prevention of tooth decay and stannous ions for efficacy in anti-plaque, anti-gingivitis, and hypersensitivity. While providing a number of benefits, however, stannous fluoride has a bitter salty (astringent) taste and is also only slightly soluble in water and accordingly does not readily dissociate to provide stannous ions. Stannous fluoride is therefore beneficially dissociated at a generally acidic pH. However, such a pH frustrates stability with other agents used in such compositions, such as the triclosan.

SUMMARY

The present invention provides oral care compositions. Embodiments include oral care compositions, comprising:
  a) a first phase comprising clinically efficacious 2,4,4'-trichloro-2'-hydroxydiphenyl ether admixed in a first orally acceptable aqueous vehicle; and
  (b) a second phase comprising stannous salt admixed in a second orally acceptable aqueous vehicle; wherein
  (c) the second phase comprises no less than 10 molar percent of soluble stannous ion respective to a mathematical sum of moles of the soluble stannous ion and moles of the stannous salt in the second phase.

In one aspect, the first phase further comprises an antibacterial-enhancing agent. Preferably the first phase has a measured pH of from about 7 to about 9, and the second phase has a measured pH of from about 3 to about 8. In various embodiments, the enhancing agent is a methylvinyl ether-maleic anhydride copolymer. In one aspect of this, the methylvinyl ether-maleic anhydride copolymer antibacterial-enhancing agent has a molecular weight from about 100 to about 1,000,000.

In another aspect, the second phase further comprises polycarboxylic acid (preferably a food grade organic acid such as citric acid, lactic acid, tartaric acid, gluconic acid, succinic acid, malic acid, fumaric acid, or combinations thereof), preferably sufficient to effectively stabilize soluble stannous ion concentration in the second phase.

In one aspect the second phase further comprises polyphosphate salt (such as disodium pyrophosphate, dipotassium pyrophosphate, tetrapotassium pyrophosphate, tetrasodium pyrophosphate, or combinations thereof).

In yet other aspects, either or both of the first and second phases further comprise a either or both of silica and a surfactant, such as sodium lauryl sulfate.

In another aspect, an oral care kit having a first chamber with a first outlet in fluid communication with the first chamber for discharge of a first dentifrice from the first chamber and a second chamber with a second outlet in fluid communication with the second chamber for discharge of a second dentifrice from the second chamber is provided with the first and second chambers respectively containing the first phase and second phase of the above-described formulations as their respective dentifrice.

In another aspect, the above formulations are made through admixing a first dentifrice and a second dentifrice according to any above formulation, and then blending together an amalgam of the first dentifrice and the second dentifrice. In one aspect of this, the first dentifrice is stored in a first enclosure after being admixed; the second dentifrice is stored in a second enclosure after being admixed; and the blending is achieved by expelling the first dentifrice from the first enclosure and expelling the second dentifrice from the second enclosure so that the first dentifrice and the second dentifrice are expelled to provide the amalgam (such as toothpaste).

In yet another aspect, any above amalgam formulation is applied to the teeth of a human or other animal subject for the purpose of cleaning their teeth.

It has been discovered that compositions and methods of this invention afford advantages over oral care compositions among known in the art. Further uses, benefits and embodiments of the present invention are apparent from the description set forth herein.

DESCRIPTION

The following definitions and non-limiting guidelines must be considered in reviewing the description of this invention set forth herein. The headings (such as "Introduction" and "Summary,") and sub-headings (such as "Compositions" and "Methods") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word 'include," and its variants, is intended to be non-limiting, such that recitation of items in a list is not to the exclusion of other like items that may also be useful in the materials, compositions, devices, and methods of this invention.

As used herein, the word "stable" and its variants references a property of a formulation where a focal chemical entity such as an element, an ion, or a molecule sustains at a desired concentration over an extended period of time and does not react with other ingredients of the oral care composition in such a manner as to not sustain the desired concentration over an extended period of time and, thereby, does not react with other ingredients of the oral care composition in such a manner as to reduce the effective amount of available desired chemical entity in the composition.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

Compositions

The present invention provides oral care compositions and methods for administration or application to, or use with, a human or other animal subject. As referred to herein, an "oral care composition" is any composition that is suitable for administration or application to the oral cavity of a human or animal subject for enhancing the health, hygiene or appearance of the subject, preferably providing such benefits as: the prevention or treatment of a condition or disorder of the teeth, gums, mucosa or other hard or soft tissue of the oral cavity; the prevention or treatment of a systemic condition or disorder; the provision of sensory, decorative or cosmetic benefits; and combinations thereof. In various preferred embodiments, an oral care composition is not intentionally swallowed, but is rather retained in the oral cavity for a time sufficient to effect the intended utility. Preferably, specific materials and compositions to be used in this invention are, accordingly, pharmaceutically- or cosmetically-acceptable. As used herein, such a "pharmaceutically acceptable", "clinically efficacious, or "cosmetically acceptable" component or "orally acceptable vehicle" is one that is suitable for use with humans and/or animals to provide the desired therapeutic, prophylactic, sensory, decorative, or cosmetic benefit without undue adverse side effects (such as toxicity, irritation, and allergic response) commensurate with a reasonable benefit/risk ratio.

In further detail, the present invention provides two phase compositions comprising clinically efficacious halogenated diphenyl ether antimicrobial (e.g., 2,4,4'-trichloro-2'-hydroxydiphenyl ether (Triclosan)) in one (a first) phase and a stannous salt (preferably stannous fluoride) in another (a second) phase where the stannous salt has effectively dissociated to provide 10 percent or more of the general stannum element in its phase as soluble stannous ion. More specifically in this regard, the second phase comprises no less than 10 molar percent of soluble stannous ion respective to a mathematical sum of moles of soluble stannous ion and moles of stannous salt in the second phase. In fuller consideration of this, a stannous salt such as stannous fluoride ($SnF_2$) is an ionic compound of the stannous ion (derived from the stannum element as symbolized by Sn in chemical nomenclature) and (now using stannous fluoride herein as a useful example, without limitation, of a stannous salt) of 2 fluoride ions (derived from the fluorine element as symbolized by F in chemical nomenclature). The stannum element is ionically provided in essentially two general ionic forms: the stannic (+4 valence) form and the stannous (+2 valence) form. The stannous fluoride molecule contains stannous ions and fluoride ions, but the stannous fluoride molecule is a white crystalline powder that is generally insoluble in alcohols and ethers and is only slightly soluble in water. Efficacy in oral care for both the stannous and fluoride ions is achieved when the stannous and fluoride ions dissociate from the stannous fluoride molecule and then proceed to chemically interact with the tooth surface and/or gum tissue. An acidic pH augments dissociation of the stannous ion (from the stannous fluoride molecule) into soluble stannous ion, and this dissociation also "frees" the fluoride ion into soluble form for interaction with the surface of the teeth. Given the relatively short time period when toothpaste is applied and brushed against the teeth and the relatively low general solubility and dissociation of stannous fluoride, an available amount of free stannous ion in the toothpaste formulation at the moment of application of toothpaste to the teeth is highly desirable. The embodiments, therefore, provide an effectively acid pH (a chemical pH of about 7 or less) with a measured pH (the pH measured when a pH probe is inserted into the stannous-fluoride-containing phase of the composition) of between about 3 and about 8.

The first phase of the composition of the invention comprises a phenolic antimicrobial, preferably a halogenated diphenylether. Preferred diphenylethers useful herein include triclosan (2,4,4'-trichloro-2'-hydroxydiphenyl ether), triclosan monophosphate or 2,2'-dihydroxy-5,5'-dibromodiphenylether. Triclosan is a particularly preferred diphenylether.

An effectively acidic pH, however, is one of several chemical conditions and/or components (such as polyphosphate and/or polyethylene glycol) that significantly reduce the efficacy of 2,4,4'-trichloro-2'-hydroxydiphenyl ether (Triclosan). In this regard, Triclosan benefits from storage at a pH of from about 7 to about 9.

In one embodiment, these contradictory pH considerations are resolved by formulating a halogenated diphenyl ether and clinically efficacious stannous salt (preferably stannous fluoride) with no less than 10 molar percent of soluble stannous ion respective to a mathematical sum of moles of the soluble stannous ion and moles of the stannous salt (stannous fluoride) in such a way that the halogenated diphenyl ether and the stannous salt (stannous fluoride) are physically separated in two separate aqueous admixtures, storing each of the two aqueous admixtures in a physically separate chamber (such as provided in a dual-compartment tube of toothpaste), and blending the two aqueous admixtures (dentifrices) together into an amalgam when the anticipated time between amalgam formation and application of the amalgam to the teeth is sufficiently minimal such that the reaction time needed for deterioration of the halogenated diphenyl ether and/or for diminishment of the soluble stannous ion is not sufficient for these detrimental effects to occur prior to use. In this regard, the first dentifrice (with the halogenated diphenyl ether) provides at least one first portion (or compositional phase) of the amalgam and the second dentifrice (having the stannous salt with no less than 10 molar percent of soluble stannous ion respective to a mathematical sum of moles of the soluble stannous ion and moles of the stannous salt) provides at least one second portion (or compositional phase) of the amalgam. However, when the first dentifrice is expelled from the first enclosure of the dual-compartment tube to provide a first portion of the amalgam (on a toothbrush) and the second dentifrice is expelled from the second enclosure of the dual-compartment tube to provide a second portion of the amalgam, the chemical properties (such as pH) within each portion of the amalgam continue to be generally independently sustained as were previously intrinsic to the respective first and second enclosures even though the two portions (two phases) are in fluid interface. The general intermixing of the phases into a common chemical property environment occurs on the tooth surface only as the two phases of the amalgam are intermixed by a brushing action. Indeed, some deposition of stannous ions, fluoride ions (or other halide ions of another stannous salt), and halogenated diphenyl ether molecules from the independent phases of the amalgam will occur on the tooth surface just prior to intermixing of the portions commensurate with actual brushing.

Orally Acceptable Carrier

The present invention provides compositions comprising an orally acceptable carrier. As used herein, an "orally acceptable carrier" or "orally acceptable vehicle" refers to a material or combination of materials that are safe for use in the compositions of the present invention, commensurate with a reasonable benefit/risk ratio, with which stannous salt (stannous fluoride) and/or halogenated diphenyl ether may be associated while retaining significant clinical efficacy. Preferably, the carrier does not substantially reduce the efficacy of the stannous salt (stannous fluoride) and/or halogenated diphenyl ether. In various embodiments, the carrier is operable to sufficiently adhere the dentifrice against surfaces within the oral cavity to which the composition is administered, without concomitant use of a dental tray, mouthpiece, tape, or similar appliance. In various preferred embodiments, an oral care composition is not intentionally swallowed, but is rather retained in the oral cavity for a time sufficient to effect the intended utility. Preferably, specific materials and compositions to be used in this invention are, accordingly, pharmaceutically- or cosmetically-acceptable. As used herein, such a "pharmaceutically acceptable" or "cosmetically acceptable" component is one that is suitable for use with humans and/or animals to provide the desired therapeutic, prophylactic, sensory, decorative, or cosmetic benefit without undue adverse side effects (such as toxicity, irritation, and allergic response) commensurate with a reasonable benefit/risk ratio.

In various embodiments, the compositions of the present invention optionally comprise a whitening agent or polishing agent. As further discussed below, a "whitening agent" is a material that is effective to effect whitening of a tooth surface to which it is applied. In various embodiments, the compositions of this invention comprise a peroxide whitening agent, comprising a peroxide compound is used.

Materials among those that are useful in carriers include adhesion agents, viscosity modifiers, diluents, surfactants, foam modulators, peroxide activators, peroxide stability agents, abrasives, pH modifying agents, humectants, mouth feel agents, sweeteners, flavorants, colorants, and combinations thereof. It is understood that while general attributes of each of the above categories of materials may differ, there may be some common attributes and any given material may serve multiple purposes within two or more of such categories of materials. Preferably, such carrier materials are selected for compatibility with the peroxide complex and with other ingredients of the composition.

In various embodiments, the carrier comprises an adhesion agent. As referred to herein, an adhesion agent is a material or combination of materials that enhance the retention of the stannous ions, fluoride ions, and halogenated diphenyl ether molecules on the oral cavity surface onto which the composition is applied. Such adhesion agents include adhesives, film forming materials, viscosity enhancers and combinations thereof. Such materials include hydrophilic organic polymers, hydrophobic organic polymers, silicone gums, silicone adhesives, silicas, and combinations thereof.

Thickening agents among those useful herein include carboxyvinyl polymers, carrageenans (also known as Irish moss and more particularly iota-carrageenan), cellulosic polymers such as hydroxyethylcellulose, carboxymethylcellulose (carmellose) and salts thereof (e.g., carmellose sodium), natural gums such as karaya, xanthan, gum arabic and tragacanth, colloidal magnesium aluminum silicate, colloidal silica, and mixtures thereof.

Viscosity modifiers among those useful herein include mineral oil, petrolatum, clays and organomodified clays, silica, and mixtures thereof. In various embodiments, such viscosity modifiers are operable to inhibit settling or separation of ingredients or to promote redispersibility upon agitation of a liquid composition.

Diluents among those useful herein include materials or combinations of materials that are operable to solubilize and/or suspend other components of the composition. In various embodiments, diluents are operable to adjust the viscosity of the composition, optionally in conjunction with viscosity modifiers (as discussed herein) and other components of the composition.

Surfactants among those useful herein include anionic, nonionic, and amphoteric surfactants. Surfactants may be used, for example, to provide enhanced stability of the formulation, to help in cleaning the oral cavity surfaces through detergency, and to provide foam upon agitation, e.g., during brushing with a dentifrice composition of the invention. Suitable anionic surfactants include water-soluble salts of $C_{8-20}$ alkyl sulfates, sulfonated monoglycerides of $C_{8-20}$ fatty acids, sarcosinates, taurates, and mixtures thereof. Illustrative examples of these and other surfactants are sodium lauryl sulfate, sodium coconut monoglyceride sulfonate, sodium lauryl sarcosinate, sodium lauryl isoethionate, sodium laureth carboxylate and sodium dodecyl benzenesulfonate, and mixtures thereof. Suitable nonionic surfactants include poloxamers, polyoxyethylene sorbitan esters, fatty alcohol ethoxylates, alkylphenol ethoxylates, tertiary amine oxides, tertiary phosphine oxides, dialkyl sulfoxides, and mixtures thereof. A preferred surfactant is sodium lauryl sulfate.

Foam modulators useful herein include materials operable to increase amount, thickness or stability of foam generated by the composition (e.g., dentifrice compositions) upon agitation. Any orally acceptable foam modulator can be used, including polyethylene glycols (PEGs), also known as polyoxyethylenes. High molecular weight PEGs are suitable, including those having an average molecular weight of about 200,000 to about 7,000,000, for example about 500,000 to about 5,000,000 or about 1,000,000 to about 2,500,000. One or more PEGs are optionally present in a total amount of about 0.1% to about 10%, for example about 0.2% to about 5% or about 0.25% to about 2%.

Humectants useful herein include polyhydric alcohols such as glycerin, sorbitol, xylitol or low molecular weight PEGs. In various embodiments, humectants are operable to prevent hardening of paste or gel compositions upon exposure to air. In various embodiments humectants also function as sweeteners.

pH modifying agents among those useful herein include acidifying agents to lower pH, basifying agents to raise pH, and buffering agents to control pH within a desired range. For example, one or more compounds selected from acidifying, basifying and buffering agents is included to provide a pH of about 3 to about 8, or in various embodiments from about 4 to about 7, from about 5 to about 6 in the first phase, first dentifrice, and/or first portion of the amalgam. One or more compounds selected from acidifying, basifying and buffering agents is also included to provide a pH of about 7 to about 9, or in various embodiments from about 8 to about 9 in the second phase, second dentifrice, and/or second portion of the amalgam. Stability of the halogenated diphenyl ether is preferably achieved with a pH of from about 7 to about 9 (preferably from about 8 to about 9). Any orally acceptable pH modifying agent can be used, including carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, etc.), imidazole, and mixtures thereof. One or more pH modifying agents are optionally present in a total amount effective to maintain the composition or individual phases and/or portions of the composition in an orally acceptable pH range.

Mouth-feel agents include materials that impart a desirable texture or other feeling during use of the composition. Such agents include bicarbonate salts, which in various embodiments impart a "clean feel" to teeth and gums due to effervescence and release of carbon dioxide. Any orally acceptable bicarbonate can be used, including (without limitation) alkali metal bicarbonates such as sodium and potassium bicarbonates, ammonium bicarbonate, and mixtures thereof.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.001% to about 5%, optionally from about 0.01% to about 1%.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20%, for example about 0.01% to about 10% or about 0.1% to about 5%.

Active Materials:

The compositions of the present invention optionally comprise additional active materials, which are operable for the prevention or treatment of a condition or disorder of hard or soft tissue of the oral cavity, the prevention or treatment of a physiological disorder or condition, or to provide a cosmetic benefit. In various embodiments, the active is a "systemic active" which is operable to treat or prevent a disorder that, in whole or in part, is not a disorder of the oral cavity. In various embodiments, the active is an "oral care active" operable to treat or prevent a disorder or provide a cosmetic benefit within the oral cavity (e.g., to the teeth, gingiva or other hard or soft tissue of the oral cavity). Oral care actives among those useful herein include whitening agents, anticaries agents, tartar control agents, antiplaque agents, periodontal actives, abrasives, breath freshening agents, malodour control agents, tooth desensitizers, salivary stimulants, and combinations thereof. It is understood that while general attributes of each of the above categories of actives may differ, there may some common attributes and any given material may serve multiple purposes within two or more of such categories of actives.

Actives useful herein are present in the compositions of the present invention in safe and effective (clinically efficacious)

amounts. A "safe and effective" and/or "clinically efficacious" amount of an active is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective amount of the active will vary with such factors as the particular condition being treated, the physical condition of the subject, the nature of concurrent therapy (if any), the specific active used, the specific dosage form, the carrier employed, and the desired dosage regimen.

Formulations which contain stannous compounds such as stannous salt (preferably stannous fluoride) exhibit excellent clinical benefits, particularly in the reduction of gingivitis but have not been widely used in aqueous oral care formulations because of stability problems as the stannous ion is unstable and tends to react with other ingredients of the oral care composition to form insoluble inactive tin compounds, thereby reducing the effective amount of available stannous ion in the composition.

A highly desired property in the embodiments is that stannous ions in the formulation are chemically stable, sustain at the desired concentration of at least 10 percent or more over an extended period of time respective to the available stannous ion, and do not react with other ingredients of the oral care composition in such a manner as to not sustain the desired concentration (of 10 percent or greater of the available stannous ion) over an extended period of time. More specifically, 10 percent of the available stannous ion references 10 molar percent of soluble stannous ion respective to a mathematical sum of moles of the soluble stannous ion in the phase having the stannous salt (preferably stannous fluoride) and moles of stannous salt (preferably stannous fluoride) molecules in that phase. Prior to dissociation of stannous ions occurring to equilibrium with the stannous salt (preferably stannous fluoride) in the phase, the number of stannous moles is defined by the amount of stannous salt (preferably stannous fluoride) initially admixed into the dentifrice phase.

As previously discussed, an acidic pH augments dissociation of the stannous ion (from the stannous salt molecule) into soluble stannous ion, and this dissociation also "frees" the fluoride ion into soluble form for interaction with the surface of the teeth. An acidic pH augments stability of the stannous ion in one embodiment. The embodiments, therefore, provide an effectively acid pH (a chemical pH of about 7 or less) with a measured pH (the pH measured when a pH probe is inserted into the stannous-fluoride-containing phase of the amalgam composition) of from about 3 to about 8 (more preferably, from about 4 to about 7).

In one embodiment, from about 0.25 to about 5 weight percent of a second salt (such as stannous chloride if stannous fluoride is the primary stannous salt) is also added to augment stability of soluble stannous ion in the primary stannous salt (preferably stannous fluoride) phase and to help sustain soluble stannous ion at not less than 10 molar percent respective to the mathematical sum of moles of soluble stannous ion and moles of stannous salt (preferably stannous fluoride) in that phase. The stannous ion sources are useful, for example, as a periodontal active, tartar control agent, anticaries agent or tooth desensitizer. Any orally acceptable stannous ion source can be used as primary and secondary stannous sources in the embodiments, such as stannous fluoride (the preferred active), stannous chloride, stannous chloride dihydrate, organic stannous carboxylate salts such as stannous formate, acetate, gluconate, lactate, tartrate, oxalate, malonate and citrate, stannous ethylene glyoxide, and mixtures thereof.

One formulation embodiment further provides an oral care composition having clinically efficacious stannous salt (preferably stannous fluoride) and an antibacterial-enhancing agent admixed into the first orally acceptable aqueous vehicle. The enhancing agents (EA) of the present invention can include those that are characterized as having utility as denture adhesives or fixatives or dental cements. The enhancing agent include polymers or copolymers, which terms are entirely generic, thus including for example oligomers, homopolymers, copolymers of two or more monomers, ionomers, block copolymers, graft copolymers, cross-linked polymers and copolymers, and the like. The EA may be natural or synthetic, and water (saliva) soluble or swellable (hydratable, hydrogel forming) polymer or copolymer. The EA can be selected to have various sizes, such as an (weight) average molecular weight (MW) of: from about 100 to about 1,000,000; from about 1,000 to about 1,000,000; or from about 2,000-2,500 to about 250,000-500,000.

The delivery enhancing groups of the EA can be any of those listed in U.S. Pat. Nos. 5,538,715 and 5,776,435, which are incorporated by reference. In various embodiments, the delivery-enhancing groups are preferably acidic such as sulfonic, phosphinic, or more preferably phosphonic or carboxylic, or a salt thereof, e.g. alkali metal or ammonium. The retention enhancing group(s) can be any organic retention-enhancing group, for example, those that have the formula —(X)n-R wherein X is O, N, S, SO, $SO_2$, P, PO or Si or the like, R is hydrophobic alkyl, alkenyl, acyl, aryl, alkaryl, aralkyl, heterocyclic or their inert-substituted derivatives, and n is zero or one or more. The aforesaid "inert-substituted derivatives", are intended to include substituents on R which are generally non-hydrophilic and do not significantly interfere with the desired functions of the EA as enhancing the delivery of the mixture (anti-bacterial agent) to, and retention thereof on, oral surfaces such as halo, e.g., Cl, Br, I, and carbo and the like.

The EA can be a synthetic anionic polymeric or linear anionic polymeric polycarboxylate having an average MW of from about 100 to about 1,000,000, or from about 1,000 to about 1,000,000, and can be present in the oral composition from about 0.0005 to about 5% by weight, from about 0.005 to about 4% by weight, or from about 0.05 to about 3% by weight. The EA can be an anionic copolymer of maleic acid or anhydride with another ethylenically unsaturated polymerizable monomer. The EA can be a copolymer of maleic acid or anhydride with methyl vinyl ether, such as any one or more of the forms of GANTREZ (available from ISP of Wayne, N.J.).

The delivery enhancing groups of the EA can also be various phosphonates. Such phosphonate-type EA's can have an average MW from about 100 to about 1,000,000 or from about 1,000 to about 1,000,000. The EA can be a polyvinyl phosphonate and/or alkali metal polyvinyl phosphonate and/or ammonium polyvinyl phosphonate of MW about 1000 or more. The phosphonate-type EA can be present in the oral composition from about 0.0005 to about 4% by weight. The EA can be a poly(β-styrenephosphonate), poly(α-styrenephosphonate), copoly(α,β-styrenephosphonate) or another copolymer of α- or β-styrenephosphonate with another polymerizable ethylenically unsaturated monomer, such as copoly (β-styrenephosphonate/vinylphosphonate). The phosphonate-type EA can have an average MW of from about 2,000 to about 30,000.

The antibacterial-enhancing agent is in the first phase (the phase having the ether) in an amount having a weight ratio of from about 0.1:1 to about 35:1, respective to the ether, optionally from about 0.15:1 to about 32:1, optionally from about 1:1 to about 10:1, optionally from about 2:1 to about 8:1, optionally from about 5:1 to about 7:1. In various embodiments, the antibacterial-enhancing agent is in the first phase in an amount having a weight ratio of from about 0.15 to about 32 respective to the halogenated diphenyl ether.

Tetrasodium pyrophosphate, the methylvinyl ether-maleic anhydride copolymer antibacterial enhancing agent, and a silica oral polishing agent are all optionally and independently admixed into the formulation in alternative embodiments of the oral care composition. In one embodiment, the methylvinyl ether-maleic anhydride copolymer antibacterial agent has the structural formula

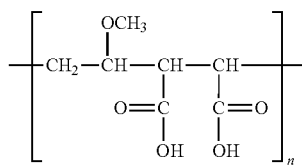

where n provides molecular weight in the agent from about 60,000 to about 500,000.

In another embodiment, the silica oral polishing agent is high cleaning silica. The compositions of the present invention optionally comprise silica abrasive in at least one of the phases. Silica is admixed into both phases of the amalgam in one embodiment. Silica is admixed overall to provide an amalgam of from about 10.00 to about 50.00 weight percent dental type precipitated amorphous hydrated silicon dioxide and from about 10.00 to about 15.00 weight percent synthetic amorphous silica. In the dual phase amalgam (having at least two portions where each of the portions is extruded from an independently stored phase) described above, silica is provided in the first phase as from about 10.00 to about 50.00 weight percent dental type precipitated amorphous hydrated silicon dioxide, from about 0.00 to about 8.00 weight percent synthetic amorphous precipitated silica, and from about 0.00 to about 8.00 weight percent synthetic amorphous precipitated silica. In the second phase, silica is provided as from about 10.00 to about 50.00 weight percent precipitated synthetic amorphous silica, from about 0.00 to about 15.00 weight percent synthetic amorphous silica, and from about 0.00 to about 8.00 weight percent synthetic amorphous precipitated silica. In various embodiments, an abrasive is useful for example as a polishing agent. Any orally acceptable abrasive can also optionally be used, but type, fineness (particle size) and amount of abrasive should be selected so that tooth enamel is not excessively abraded in normal use of the composition. Suitable abrasives include silica, for example in the form of silica gel, hydrated silica or precipitated silica, alumina, insoluble phosphates, calcium carbonate, resinous abrasives such as urea-formaldehyde condensation products, and mixtures thereof. Among insoluble phosphates useful as abrasives are polyphosphates such as orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. One or more abrasives are optionally present in an abrasive effective total amount, typically about 5% to about 70%, for example about 10% to about 50% or about 15% to about 30% by weight of the composition. Average particle size of an abrasive, if present, is generally about 0.1 to about 30 microns, for example about 1 to about 20 microns or about 5 to about 15 microns. The use of silica is preferred to reduce staining of the teeth due to the stannous salt (preferably stannous fluoride).

The active ingredients in one embodiment include both clinically efficacious stannous salt (preferably stannous fluoride) with a clinically efficacious anticalculus agent for tartar control. Tartar control (anticalculus) agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J. One or more anticalculus agents are optionally present in an anticalculus effective total amount, typically about 0.001% to about 50%, for example about 0.05% to about 25% or about 0.1% to about 15%.

In optional alternative embodiments, any pyrophosphate salt such as dialkali metal pyrophosphates, tetraalkali metal pyrophosphates, and combinations of these are used. Specific compounds and formulations of these salts include disodium pyrophosphate, dipotassium pyrophosphate, tetrapotassium pyrophosphate, tetrasodium pyrophosphate, and combinations thereof.

The compositions of the present invention comprise an optional antimicrobial (e.g., antibacterial) agent to further augment the 2,4,4'-trichloro-2'-hydroxydiphenyl ether. Any orally acceptable antimicrobial agent can be used such as 8-hydroxyquinoline and salts thereof; zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride,); bisguanides, such as chlorhexidine digluconate, hexetidine, octenidine, and alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; magnolia extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of useful antibacterial agents is provided in U.S. Pat. No. 5,776,435, Gaffar, et al., issued Jul. 7, 1998.

The compositions of the present invention optionally comprise a saliva stimulating agent, useful for example in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in a saliva stimulating effective total amount.

The compositions of the present invention optionally comprise a breath freshening agent. Any orally acceptable breath freshening agent can be used, including without limitation zinc salts such as zinc gluconate, zinc citrate and zinc chlorite, α-ionone, and mixtures thereof. One or more breath freshening agents are optionally present in a breath freshening effective total amount.

The compositions of the present invention optionally comprise an antiplaque (e.g., plaque disrupting) agent. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates, and mixtures thereof.

The compositions of the present invention optionally comprise an anti-inflammatory agent. Any orally acceptable anti-inflammatory agent can be used, including steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone, and mixtures thereof.

The compositions of the present invention optionally comprise an $H_2$ antagonist. $H_2$ antagonists useful herein include cimetidine, etintidine, ranitidine, ICIA-5165, tiotidine, ORF-17578, lupititidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, HB-408.4, and mixtures thereof.

The compositions of the present invention optionally comprise a desensitizing agent. Desensitizing agents useful herein include potassium citrate, potassium chloride, potassium tartrate, potassium bicarbonate, potassium oxalate, potassium nitrate, strontium salts, and mixtures thereof. Alternatively or in addition a local or systemic analgesic such as aspirin, codeine, acetaminophen, sodium salicylate or triethanolamine salicylate can be used.

The compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), fish oil (including components thereof such as omega-3 (N-3) polyunsaturated fatty acids, eicosapentaenoic acid and docosahexaenoic acid), coenzyme Q10, and mixtures thereof.

The compositions of the present invention optionally comprise proteins. Suitable proteins include milk proteins and enzymes such as peroxide-producing enzymes, amylase, plaque-disrupting agents such as papain, glucoamylase, glucose oxidase, and "next generation" enzymes."

In one embodiment, an additional fluoride ion source such as an amine fluoride, more specifically, olaflur (N'-octadecyltrimethylendiamine-N,N,N'-tris(2-ethanol)-dihydrofluoride) is intermixed into either of the phases to further augment fluoride ion concentration in the applied dentifrice.

In further detail, one two-phase amalgam formulation embodiment provides a differentiated phase oral care composition having clinically efficacious 2,4,4'-trichloro-2'-hydroxydiphenyl ether admixed in a first orally acceptable aqueous vehicle as a first phase and stannous fluoride admixed in a second orally acceptable aqueous vehicle (having no less than 10 molar percent of soluble stannous ion respective to a mathematical sum of moles of the soluble stannous ion and moles of the stannous fluoride) as a second phase where (a) the first phase is admixed to comprise an aqueous blend of from about 8 to about 25 weight percent synthetic glycerin, from about 0.5 to about 1.5 weight percent sodium carboxymethyl cellulose, from about 0.2 to about 1.2 weight percent iota carrageenan gum, from about 0.0001 to about 0.8 weight percent sodium saccharin, not greater than 1.5 weight percent titanium dioxide, from about 8 to about 25 weight percent sorbitol, from about 0.5 to about 8 weight percent methyl vinyl ether/maleic anhydride copolymer, sodium hydroxide sufficient for providing a measured pH of from about 7 to about 9 in said first phase, from about 8 to about 25 weight percent silica, not greater than 5 weight percent sodium bicarbonate, from about 0.5 to about 2 weight percent flavor oil, from about 0 to about 3 weight percent propylene glycol, from about 0.2 to about 1 weight percent 2,4,4'-trichloro-2'-hydroxydiphenyl ether, from about 0.5 to about 4 weight percent sodium lauryl sulfate, and from about 0.243 to about 0.486 weight percent sodium fluoride; and (b) the second phase is admixed to comprise an aqueous blend of, from about 0.05 to about 1 weight percent anhydrous citric acid, from about 0.5 to about 5 weight percent trisodium citrate dihydrate, from about 0.05 to about 2 weight percent stannous fluoride, from about 0.25 to about 5 weight percent stannous chloride dihydrate, not greater than 0.243 weight percent sodium fluoride, from about 10 to about 40 weight percent synthetic glycerin, from about 0.5 to about 1.5 weight percent sodium carboxymethyl cellulose gum, from about 0.2 to about 1 weight percent xanthan gum, from about 0.001 to about 0.8 weight percent sodium saccharin, not greater than 0.5 weight percent 2,4,4'-trichloro-2'-hydroxydiphenyl ether, from about 0.005 to about 1 weight percent tetrasodium pyrophosphate, from about 0.2 to about 4 weight percent polyoxypropylene-polyoxyethylene block copolymer having an average molecular weight of about 12,600, from about 0.05 to about 10 weight percent hydrogenated castor oil, not greater than 4% weight percent methyl vinyl ether/maleic anhydride copolymer, from about 0.0005 to about 2 weight percent color dye, not greater than 1.5 weight percent titanium dioxide,
from about 0.5 to about 4 weight percent sodium lauryl sulfate,
from about 0.5 to about 2 weight percent flavor oil, and
from about 8 to about 35 weight percent silica;
where the methylvinyl ether-maleic anhydride copolymer has the structural formula

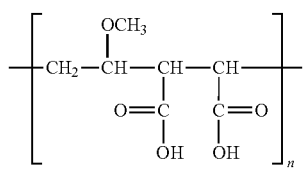

where n provides molecular weight in the agent from about 60,000 to about 500,000.

In various embodiments, the compositions of the present invention also comprise an additional taste improvement component selected from the group consisting of castor oil, sodium bicarbonate, and mixtures thereof.

Methods of Manufacture:

The compositions of the present invention are made by any of a variety of methods, including adding and mixing the ingredients of the composition in a suitable vessel such as a stainless steel tank provided with a mixer. In one embodiment, the 2,4,4'-trichloro-2'-hydroxydiphenyl ether is admixed into a first orally acceptable aqueous vehicle to provide a first phase of a dentifrice; the stannous salt (preferably stannous fluoride) is admixed into a second orally acceptable aqueous vehicle to provide a second phase of the dentifrice; the first phase is stored in a first enclosure; the second phase is stored in a second enclosure; and the first phase is expelled from the first enclosure and the second phase is expelled from the second enclosure just prior to application to the teeth so that the first phase and the second phase are expelled to provide an amalgam where the amalgam has at least one first portion comprising the first phase, the amalgam has at least one second portion comprising the second phase, and each first portion is in fluid interface with at least one second portion. This embodiment is preferably provided to the consumer in the form of an oral care kit providing (a) a first chamber (the first storage enclosure for storing the first phase of the amalgam) having a first outlet in fluid communication with the first chamber for discharge of a first dentifrice (the first phase of the amalgam) from the first chamber and (b) a second chamber (the second storage enclosure for storing the second phase of the amalgam) having a second outlet in fluid communication with the second chamber for discharge of a second dentifrice (the second phase of the amalgam) from the second chamber. The second outlet is proximate to the first outlet so that, during simultaneous discharge of the first dentifrice from the first chamber through the first outlet and of the second dentifrice from the second chamber through the second outlet, discharged first dentifrice fluidly interfaces with discharged second dentifrice to form the amalgam. Such a system is also denoted herein as a dual compartment toothpaste tube. Preferably, equal amounts of each phase are delivered into the amalgam so that the consumer has a convenient basis for ascertaining that both phases are being delivered and that rapid intermixing of the phases will occur as the amalgam is brushed against the teeth.

Additional ingredients such as flavorant, coloring or sweeteners are added at any point during the mixing process but in various embodiments such ingredients are preferably added last or close to last.

Methods

The present invention provides methods for cleaning and treating a tooth surface using compositions according to the present invention. As referred to herein, "tooth" or "teeth" refers to natural teeth, dentures, dental plates, fillings, caps, crowns, bridges, dental implants, and the like, and any other hard surfaced dental prosthesis either permanently or temporarily fixed within the oral cavity.

Preferably methods of use comprise applying a composition of the present invention to the tooth surface. As referred to herein, "applying" refers to any method by which a compositional embodiment is placed in contact with the tooth surface. Such methods, in various embodiments, comprise direct application of a composition by such methods as painting and brushing. Suitable application devices include toothbrushes.

In various embodiments, it is preferred that the subject does not eat or drink while the oral care composition is in contact with the dental surface. The oral care composition can be removed as and when required, at will, by an employment of standard oral hygiene procedures such as brushing or by rinsing, e.g., with a mouthwash.

In various embodiments, compositions of the present invention are also used for the treatment or prevention of disorders in the oral cavity, including cavity prevention, whitening, plaque prevention or reduction, gingivitis prevention or reduction, tartar control, sensitivity prevention or reduction, breath malodor prevention or reduction, and stain prevention. Compositions of the present invention may also be used for the treatment or prevention of systemic disorders, such as the improvement of overall systemic health characterized by a reduction in risk of development of systemic diseases, such as cardiovascular disease, stroke, diabetes, severe respiratory infection, premature and low birth weight infants (including associated post-partum dysfunction in neurologic/developmental function), and associated increased risk of mortality. Such methods include those disclosed in U.S. Patent Publication 2003/0206874, Doyle et al., published Nov. 6, 2003.

The described embodiments minimize the astringent taste traditionally associated with stannous oral care compositions and incorporate high cleaning silica to reduce tooth staining. In the dual stream delivery system embodiments afforded by the dual-compartment tube, one side of the system delivers the stannous ingredient and the second side delivers tartar control benefits along with flavorants that successfully mask stannous astringency.

The present invention is further illustrated through the following non-limiting examples.

EXAMPLE 1

Preparation of Formulas for Testing

Two dual tube dentifrice formulations (Formula A and Formula B) and two control dentifrice formulations are prepared as indicated in Table 1.

TABLE 1

| Ingredient | Formula A | Formula B | Formula C (Control) | Formula D (Control) |
|---|---|---|---|---|
| Tube type | Dual tube | Dual tube | Single tube | Single tube |
| Side | Side 1 | Side 1 | NA | NA |
| Synthetic Glycerin | 10.00 | 10.00 | 20.00 | 22.00 |
| Sodium Carboxymethyl Cellulose | 1.10 | 1.10 | 1.10 | |
| Iota Carrageenan gum | 0.40 | 0.40 | 0.40 | |
| Sodium Saccharin | 0.30 | .3 | .3 | 0.20 |
| titanium dioxide | 0.50 | 0.50 | 0.50 | |
| Sorbitol | 13.40 | 13.40 | 20.85 | |
| Water | 10.13 | 4.96 | 11.94 | 22.00 |
| Gantrez * (13% active) | 30.00 | 30.00 | 15.00 | |
| Sodium Hydroxide ** | ** | ** | 1.20 | |
| Silica | 22.00 | 22.00 | 21.50 | |
| Sodium Bicarbonate | 3.50 | 3.50 | | |
| flavor | 1.20 | 1.20 | 1.00 | 0.89 |
| propylene Glycol | 1.70 | 1.70 | 0.50 | |
| Triclosan | 0.60 | 0.60 | 0.30 | |
| Sodium lauryl Sulfate (29% active) | 5.17 | 10.34 | 5.17 | 4.14 |
| Sodium fluoride | | | 0.24 | |
| Sodium monofluorophosphate | | | | 0.76 |
| tetrasodium pyrophosphate | | | | 1.00 |
| Sodium Carboxymethyl Cellulose - 7 | | | | 0.25 |
| Dicalcium phospate | | | | 48.76 |
| pH (10% solution) | 8.61 | 8.83 | | |

| Ingredient | Formula A | Formula B | Formula C (Control) | Formula D (Control) |
|---|---|---|---|---|
| Tube type | Dual tube | Dual tube | Single tube | Single tube |
| Side | Side 2 | Side 2 | NA | NA |
| Water | 21.73 | 26.90 | | |
| Anhydrous Citric acid | 0.53 | 0.53 | | |
| trisodium Citrate dihydrate | 2.66 | 2.66 | | |
| Stannous fluoride | 0.91 | 0.91 | | |
| Stannous Chloride dihydrate | 0.60 | 0.60 | | |
| Synthetic Glycerin | 31.45 | 31.45 | | |
| Sodium Carboxymethyl Cellulose gum | 0.80 | 0.80 | | |
| xanthan gum | 0.50 | 0.50 | | |
| Sodium Saccharin | 0.40 | 0.40 | | |
| tetrasodium pyrophosphate | 0.50 | 0.50 | | |
| Pluronic F27 foaming agent | 2.00 | 2.00 | | |
| Polyoxyl 40 hydrogenated Castor oil | 6.00 | 6.00 | | |
| Green color solution | 0.05 | 0.05 | | |
| Sodium lauryl Sulfate liquid (29%) | 5.17 | 0.00 | | |
| flavor | 1.20 | 1.20 | | |

TABLE 1-continued

| | | |
|---|---|---|
| Silica | 25.50 | 25.50 |
| pH 10% solution | 4.56 | 4.63 |
| combined pH of both phases upon intermixing (10% solution) | 6.81 | 7.04 |

\* Gantrez: Methyl vinyl ether/maleic anhydride copolymer
\*\* amount necessary to adjust pH to required range In vitro Efficacy—Triclosan Uptake onto HAP Disks An uptake study is used to determine triclosan deposition onto tooth-like surfaces. It involves applying of dentifrice slurry on hydroxyapatite disks for a set amount of time. The active taken onto the disk during the first step is then solubilized and analyzed by HPLC.

Chemicals used in the test include:
Formula (Table 1)
Formula B (Table 1)
Formula C (Table 1)
Deionized water
Hydroxyapatite disks
200 proof ethanol Hydroxyapatite disks in separate tubes are coated with clarified saliva (centrifuged at 10K RPM for 10 minutes and sterilized for 1 hour with ultra-violet light) and incubated overnight in a shaking water bath at 37° C. Independent dentifrice slurries are made by combining one part dentifrice (of each of Formulas A, B, and C) to, in each sample, two part deionized water with thorough mixing for 30 minutes. Once slurries are ready, the saliva coated sterilized disks are removed from the water bath, the saliva is aspirated from the tubes, and 1 ml of the appropriate slurry treatment is added to the tubes with the disks. Samples are tested against a positive control of Formula C (Colgate TOTAL™) for triclosan uptake as follows. Treated disks are incubated for one hour in a shaking water bath at 37° C. Once the incubation period is completed, the treatment slurry is aspirated off of the disks, the disks are each rinsed with 5 ml of deionized water, and the disks are vortexed. This rinsing process is repeated three times. After the final (third) rinse, all water is aspirated off of the disks, and the disks are each transferred to a new tube. 1 mL of 200 proof ethanol is placed onto each disk, and the tube and disk are placed in a shaking water bath at ambient temperature for one hour. During this time, if any triclosan is taken unto the disk, it is solubilized by the ethanol. After the incubation period, the ethanol solution from each tube is transferred into an HPLC vial, sealed, and analyzed.

Triclosan uptake (micrograms/disk) is measured as:
Formula A: 30.2
Formula B: 46.2
Formula C (Control) 54.0

The measured indices signify that Formula B shows statistically comparable Triclosan Uptake to Formula C (the control). Therefore, stannous in the dual-tube formulation of Formula B does not compromise the triclosan efficacy of Formula B in comparison to Formula C.

Clinical Efficacy (Plaque)—Modified Gingival Margin Plaque Index Determination (MGMPI) Methodology A group of panelists are given a complete oral exam and thorough dental cleaning/prophy, and then instructed to use washout toothpaste (Colgate Dental Cream (CDC)) for 1 week prior to any test treatments. Upon arrival to the test site, each panelist brushes their teeth with the CDC Dental Cream and is then given 1.5 g of a test toothpaste (Formula B, C, or D from Table 1) to brush with for one (1) minute. After brushing, each panelist rinses their teeth with water. Each panelist then rinses their teeth with 10 ml of concentrated, red plaque disclosing solution (commercially available) for 30 seconds. Baseline gingival margin plaque score is evaluated. The panelists are then instructed to refrain from any oral hygiene for a 24-hour test period. After this period, each panelist returns to the clinical site and rinses again with 10 ml of concentrated red disclosing solution. The dentist re-evaluates the panelists and determines a second gingival margin plaque score. This second gingival margin plaque score is compared to the baseline gingival margin plaque score to determine the change (delta) in plaque build up. This delta plaque score is used to compare each Formula (B, C, or D) in treatment and determine its plaque reduction efficacy. The results indicate percentage reduction in gingival Plaque as follows:

Formula B 41.4
Formula C (control) 35.7
Formula D (control) 0.0

The results indicate that the dual-tube formulation of Formula B performed statistically better than Formula D, and at least equal to Formula C (directionally better) in terms of plaque efficacy.

In vitro Efficacy—Hypersensitivity

A Dentin disks brush study is conducted on the formulations of Formulas B, C, and D and the. The purpose of this study is to explore the additional benefit of sensitivity due to stannous salt (preferably stannous fluoride). Dentinal hypersensitivity is defined as acute, localized tooth pain in response to physical stimulation of the dentine surface by thermal, osmotic and tactile stimulation of the exposed dentin. In this regard, exposure of the dentine, which is generally due to recession of the gums, or loss of enamel, frequently leads to hypersensitivity. The exposed dentinal tubules provide a pathway for transmission of fluid flow to the pulpal nerves, the transmission induced by changes in temperature, pressure and ionic gradients. Tin salts such as stannous fluoride have been indicated clinically to be efficacious in the reduction of dentinal hypersensitivity.

The dentine disks are prepared and treated. Sample preparation involves cutting and citric acid etching of the dentine disks prior to treatment. Treatment consists of brushing the disks with the test sample (any of Formulas B, D, or D as appropriate) three times a day for five days. The disks are stored in PBS when not being treated. A triplicate set of samples are prepared and submitted for study. A duplicate set of the treated disks and control disks are prepared for SEM examination by mounting on aluminum SEM holders followed by a brief (<30 second) Au sputter. ESCA and SEM are used to characterize the treated dentin disks. ESCA is used to determine the surface composition, while SEM is used to obtain images of the disk surface, and provide evidence of tubular occlusion.

Results are indicated in Table 2.

TABLE 2

| Element (atomic %) | Formula D (control) | Formula C (control) | Formula B |
|---|---|---|---|
| C | 42.45 | 37.09 | 38.20 |
| O | 34.83 | 39.67 | 40.51 |

TABLE 2-continued

| Element (atomic %) | Formula D (control) | Formula C (control) | Formula B |
|---|---|---|---|
| N | 9.39 | 6.67 | 5.80 |
| Ca | 6.73 | 3.88 | 5.27 |
| P | 5.48 | 2.48 | 4.20 |
| Na | 0.45 | 0.79 | 1.09 |
| Si | 0.50 | 9.22 | 3.69 |
| Sn | Not detected | Not detected | 1.06 |
| F | 0.33 | Note detected | 0.18 |

The results of Table 2 indicate that deposition of tin (stannous derivative) compounds on dentin surfaces is detected for the dual tube formulation of Formula B (Triclosan plus stannous fluoride), and tin is not detected for either of control Formulas C or D. The result of the deposition of tin is in occlusion of dentinal tubules, which translates to hypersensitivity efficacy.

Flavor Evaluation

Stannous is known for its astringent taste, and a great deal of effort has been placed over the years to develop acceptable flavors for stannous-containing dentifrice. The inventors have also found that addition of castor oil and sodium bicarbonate, contribute significantly to taste improvement. Dentifrices based on Formula B (Table 1) are compared with different approaches to use of castor oil and sodium bicarbonate as shown in Table 3. A panelist evaluates each of the formulations of Table 3, and the panelists' subjective evaluation is noted in Table 3.

TABLE 3

| Formula | Evaluation |
|---|---|
| Formula B w/o castor oil and w/o sodium bicarbonate | Bad |
| Formula B w/o castor oil and w sodium bicarbonate | Bad |
| Formula B w castor oil and w/o sodium bicarbonate | Acceptable |
| Formula B | Good |

Results indicate the best flavor evaluation for Formula B as indicated in Table 1.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. An oral care composition, comprising:
(a) a first phase comprising a safe and effective amount of a halogenated diphenyl ether anti-microbial and a first orally acceptable aqueous vehicle; and
(b) a second phase comprising a stannous salt, a polycarboxylic acid, and a second orally acceptable aqueous vehicle;
wherein said second phase comprises no less than 10 molar percent of soluble stannous ion respective to a mathematical of moles of said soluble stannous ion and moles of said stannous salt in said second phase;

wherein said polycarboxylic acid is selected from the group consisting of citric acid, lactic acid, tartaric acid, succinic acid, malic acid, fumaric acid and combinations thereof;

wherein said second phase further comprise a silica abrasive and does not contain a peroxide whitening agent;

wherein said composition further comprises sodium lauryl sulfate; where said sodium lauryl sulfate is substantially contained in said first phase thereby increasing uptake of said halogenated diphenyl ether anti-microbial, and wherein the polycarboxylic acid is present in an amount sufficient to effectively stabilize soluble stannous ion concentration in said second phase.

2. An oral care composition according to claim 1, wherein said halogenated diphenyl ether is 2,4,4'-trichloro-2'-hydroxydiphenyl ether.

3. An oral care composition according to claim 2, further comprising a methylvinyl ether-maleic anhydride copolymer having a molecular weight from about 100 to about 1,000,000.

4. An oral care composition according to claim 1 wherein said second phase further comprises from about 0.25 to about 5 weight percent stannous chloride.

5. An oral care composition according to claim 1 wherein said second phase further comprises polyphosphate salt.

6. An oral care composition according to claim 5, wherein said polyphosphate salt is selected from the group consisting of dialkali metal pyrophosphates, tera alkali metal pyrophosphates, and combinations thereof.

7. An oral care composition according to claim 6, wherein said polyphosphate salt is selected from the group consisting of disodium pyrophosphate, dipotassium pyrophosphate, tetrapotassium pyrophosphate, tetrasodium pyrophosphate, and combinations thereof.

8. An oral care composition according to claim 1, wherein said first phase further comprises silica.

9. An oral care kit, comprising:
(a) a first chamber having a first outlet in fluid communication with said first chamber for discharge of a first phase of an oral care composition from said first chamber; and
(b) a second chamber having a second outlet in fluid communication with said second chamber for discharge of a second phase of said oral care composition from said second chamber; wherein said first phase comprises a safe and effective amount of a halogenated diphenyl ether anti-microbial and a first orally acceptable aqueous vehicle; and said second phase comprising a stannous salt and a polycarboxylic organic acid, in a second orally acceptable aqueous vehicle;

wherein said polycarboxylic acid is selected from the group consisting of citric acid, lactic acid, tartaric acid, succinic acid, malic acid, fumaric acid and combinations thereof, said second phase comprises no less than 10 molar percent of soluble stannous ion respective to a mathematical of moles of said soluble stannous ion and moles of said stannous salt in said second phase;

wherein said second outlet is proximate to said first outlet so that, during simultaneous discharge of said first phase from said first chamber through said first outlet and of said second phase from said second chamber through said second outlet, said discharged first phase fluidly interferes with discharged second phase to yield an amalgam such that said first phase provides at least one first portion of said amalgam, said second phase provides at least one second portion of said amalgam, and said at least one said first portion is in fluid interface with said at least one said second portion;

wherein said second phase further comprises a silica abrasive and does not contain a peroxide whitening agent;

wherein said composition further comprises sodium lauryl sulfate; where said sodium lauryl sulfate is substantially contained in said first phase thereby increasing uptake of said halogenated diphenyl ether anti-microbial, and wherein the polycarboxylic acid is present in an amount sufficient to effectively stabilize soluble stannous ion concentration in said second phase.

10. An oral care kit according to claim 9, wherein said halogenated diphenyl ether is 2,4,4'-trichloro-2'-hydroxydiphenyl ether.

11. An oral care oral care kit according to claim 9, wherein said first phase further comprises a methyl vinyl ether-maleic anhydride copolymer antibacterial-enhancing agent for said ether admixed into said first orally acceptable aqueous vehicle, and said first phase has a local pH of from about 7 to about 9, and said second phase has a local pH of from about 3 to about 8.

12. An oral care kit according to claim 11, wherein said methylvinyl ether-maleic anhydride copolymer antibacterial-enhancing agent has a molecular weight from about 100 to about 1,000,000.

13. An oral care kit according to claim 9 wherein said second phase further comprises from about 0.25 to about 5 weight percent stannous chloride.

14. An oral care kit according to claim 9 wherein said second phase further comprises a polyphosphate salt selected from the group consisting of dialkali metal pyrophosphates, tetraalkali metal pyrophosphates, and mixtures thereof.

15. An oral care kit according to claim 14 wherein said polyphosphate salt is selected from the group consisting of disodium pyrophosphate, dipotassium pyrophosphate, tetrapotassium pyrophosphate, tetrasodium pyrophosphate, and combinations thereof.

16. An oral care kit according to claim 9 wherein said simultaneous discharge of said first phase from said first chamber through said first outlet and said second phase from said second chamber through said second outlet provide essentially equivalent volumetric flows of said discharged first phase and said discharged second phase.

17. An oral care composition according to claim 3, wherein said second phase further comprises from about 0.25 to about 5 weight percent stannous chloride, wherein said second phase further comprises polyphosphate salt which is selected from the group consisting of dialkali metal pyrophosphates, tetra alkali metal pyrophosphates, and combinations thereof.

18. An oral care composition according to claim 17, wherein said first phase further comprises silica and sodium bicarbonate.

19. The oral care composition of claim 18, wherein said first phase has a local pH of from about 7 to about 9, and said second phase has a local pH of from about 3 to about 8.

20. The oral care composition of claim 1, wherein said first phase has a local pH of from about 7 to about 9, and said second phase has a local pH of from about 3 to about 8.

* * * * *